US00PP09249P

United States Patent [19]

Egger

[11] Patent Number: Plant 9,249

[45] Date of Patent: Aug. 15, 1995

[54] LONGIFLORUM × ASIATIC HYBRID LILY PLANT NAMED 'CEB SUN'

[75] Inventor: Donald L. Egger, Aurora, Oreg.

[73] Assignee: Cebeco Lilies, Inc., Aurora, Oreg.

[21] Appl. No.: 333,495

[22] Filed: Nov. 2, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Klarquist Sparkman Campbell Leigh & Whinston

[57] ABSTRACT

A new and distinct lily hybrid named 'Ceb Sun' characterized by upright, large, yellow flowers with thick petals on tall, strong stems excellent for cut flower production.

1 Drawing Sheet

BACKGROUND OF THE INVENTION

The present invention comprises a new and distinct cultivar of Lily hybrid, referred to commercially as a *Longiflorum-Asiatic* Lily Hybrid, referred to by the cultivar name 'Ceb Sun'.

This invention is the product of a controlled breeding program in Aurora, Ore. The seed parent was GH-403, a proprietary non-released plant. The pollen parent was AM #2, another proprietary non-released plant.

The *Longiflorum-Asiatic* cross is relatively new to the trade. This type of cross was originally made to create colored *Lilium longiflorum* hybrids. Instead, due to the difficulty in crossing back to *L. longiflorum,* the plants that were developed had to be crossed with Asiatic lilies. As such, the results look more like Asiatic lilies. The resulting hybrids often have several advantages, not necessarily in combination, over an Asiatic lily: (1) often larger flowers; (2) often larger, waxier leaves; (3) hybrid vigor; (4) lower susceptibility to scorch; (5) excellent flower texture and substance; (6) more virus resistance; (7) new and clearer colors; and (8) stronger, sturdier stems.

This invention has not been observed under all possible environmental conditions. The phenotype may vary significantly with variations in environment such as temperature, light intensity, and day length, without, however, any variation in genotype. The following traits have been repeatedly observed in asexually propagated progeny and are determined to be the basic characteristics of this invention which in combination distinguish this lily as a new and distinct cultivar: (1) large, upright clear yellow flowers with a lighter blush and some maroon spots; (2) thick tepals which strongly overlap; (3) large yellow buds; (4) tall, strong stems for cut flowers; and (5) excellent vase life. Bulbs of this plant may be precooled and forced out of season for very uniform cut flower production.

To the inventor's knowledge, there are no other *Longiflorum-Asiatic* lily hybrids with this color flower suitable for cut flower forcing on the market.

Asexual reproduction of this new variety has been initially and subsequently accomplished at Cebeco Lilies, Inc. in Aurora, Ore., by scaling and tissue culture. The resulting plants have shown that the above-mentioned unique features are stable and reproduce true to type in each successive propagation.

Figure 2:
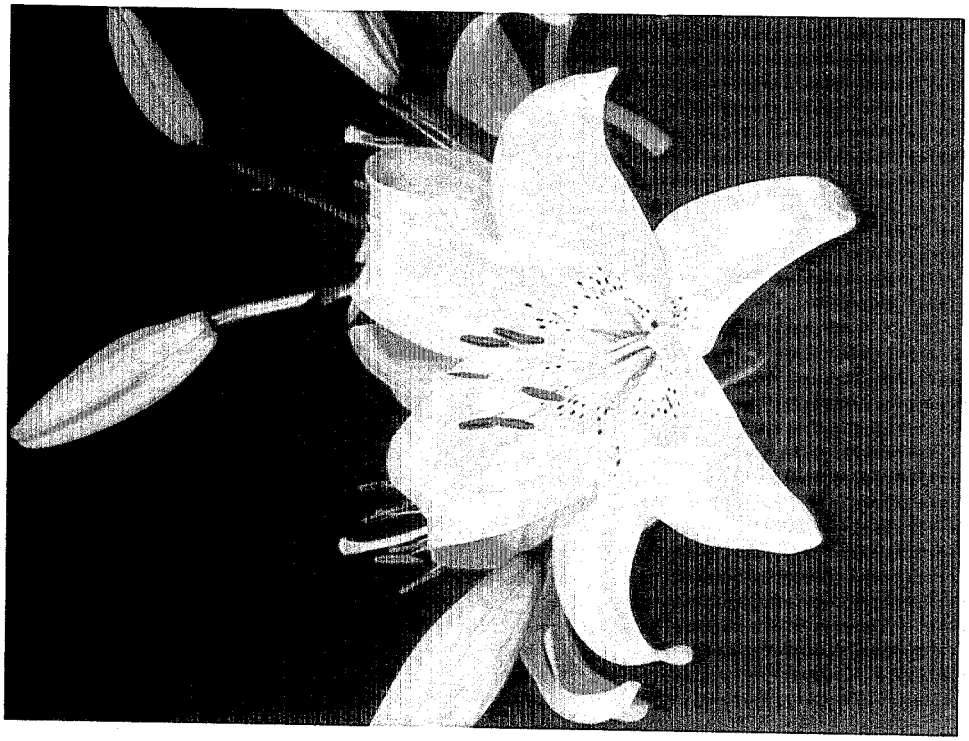
FIG. 2 is a close-up photograph which illustrates in greater detail a single flower of the new plant.
Figure 1:
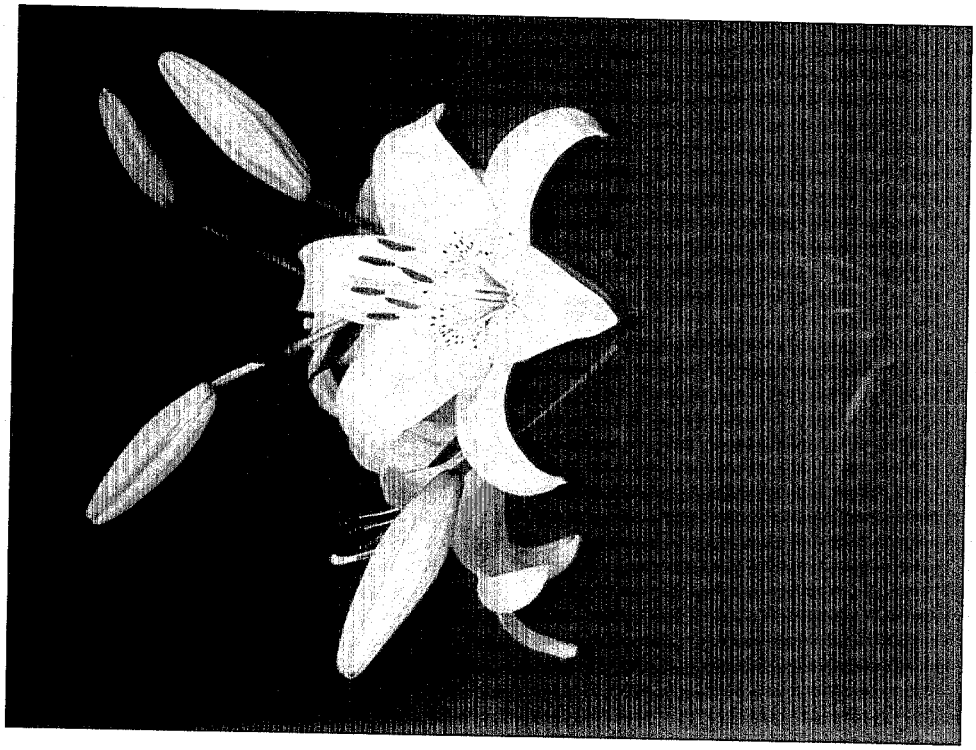
FIG. 1 is a photograph showing the 'Ceb Sun' lily.

The photographs of the drawing were taken in August 1993 in a studio and illustrate the typical flower and foliage form, with color being as true as is reasonably possible in this type of color photograph.

DETAILED DESCRIPTION

The following is a detailed description of the invention based on plants produced under commercial practices in the Cebeco Lilies, Inc. greenhouses in Aurora, Ore. in July 1993. Color references are made to The Royal Horticultural Society Colour Chart (RHS), except where the context indicates a term having its ordinary dictionary meaning.

THE PLANT

Origin: Seedling.

Parentage:

*Seed parent.*—GH-403.

*Pollen parent.*—AM #2.

Commercial classification: Upright *Longiflorum-Asiatic* hybrid, cut flower type.

Classification: Division VIII, according to the Horticultural Classification of Lilies by The Royal Horticultural Society of London.

Form: Single erect stem bearing terminal cluster of flowers.

Height: About 115 cm. from the top of the soil to the top of the flowers from bulbs of 12–14 cm. in circumference.

Growth habit: Vigorous, upright and rigid.

Foliage:

*Arrangement.*—Spiral.

*Quantity.*—Less than average.

*Leaf size.*—Large. To about 16 cm. long and about 4 cm. wide.

*Leaf shape.*—Lanceolate.

*Texture.*—Leathery.

*Aspect.*—Glossy.

*Color.*—Medium green on both sides, closest to 147A.

Bulbs:

*Size.*—Variable, ranging to about 12–14 cm. in circumference as used commercially.

*Color.*—White.

THE BUD

Size: Large, to about 11 cm. long and 3.5 cm. wide just prior to opening.

Shape: Narrow ovoid. The bud is at a slight tilt until mature.

Rate of opening: The mature bud opens slowly in response to light.

Color: Yellow. Yellow Group 8A-B.

THE FLOWER

Blooming habit: Annually, once and early season.

Days to bloom: Flowers approximately 81 days after spring greenhouse planting under typical commercial flower forcing conditions of 15° Celsius night time temperatures.

Inflorescence size: About 18 cm. high and 30 cm. wide when there are five flowers present.

Flower size: Large.

*Diameter.*—About 22.5 cm.

*Depth.*—About 6 cm.

Borne: In an umbel or modified raceme of 5 to 10 flowers from bulbs 12–14 cm. in circumference.

Shape: When the flower first opens it is bowl-shaped. Later, the shape flattens out and the tepals reflex slightly at the tips.

Tepalage:

*Number.*—Six.

*Arrangement.*—Imbricated.

*Shape.*—Ovate.

*Texture.*—Spongy, thick.

*Aspect.*—Satiny.

*Size.*—Length: About 12 cm. Width: Inner tepals — about 6 cm. Outer tepals — about 4.2 cm. Depth of imbrication: About 19 mm.

*Nectary.*—About 3 cm. long; yellow green; pubescent; with the channels close together.

*Projections.*—Few, inconspicuous, raised channels or lines, papillose.

*Spots.*—Moderate in number; large; raised; long oval in shape; located above the nectary and forming a dark margin along the lower 2 cm. above the claw of the inner tepals; maroon, Grayed-Purple Group 187B.

*Blush.*—Light yellow, Yellow Group 8C lightening to 11D with age; located around the nectary and extending up along the midrib.

*Color.*—Topside: Yellow. Yellow Group 9A lightening to 7 D with age. Topside base: Light yellow. Yellow Group 8C lightening to 11D with age. Bottomside: Yellow. Yellow Group 9A lightens to 8D with age except edges. Midrib is lighter.

*Discoloration.*—Slightly lighter color with age.

*Fragrance.*—Slight.

*Lasting quality.*—Excellent.

Pedicel:

*Length.*—Varies from about 5–20 cm.

*Color.*—Yellow-green with lightly mottled with red purple.

*Orientation.*—Ascending upwardly from about 40° from the horizontal.

THE REPRODUCTIVE ORGANS

Stamens:

*Number.*—Six, typical of the genus Lilium.

*Anthers before dehiscence.*—Size: About 2.5 cm. Color: Light brown. Grayed-Orange Group 177C.

*Filaments.*—Length: About 80 mm. Color: Greenish yellow. Green-Yellow Group 1D.

*Pollen.*—Color: Orange. Grayed-Orange Group 168B.

Pistil:

*Number.*—One.

*Style.*—Length: About 72 mm. Color: Green-Yellow Group 1A to 1D at the base.

*Stigma.*—Color: Yellow. Yellow Group 5C.

THE FRUIT

Fertility: The fruit is of low fertility.

Shape: Ovoid.

Color at maturity: Soft Brown.

I claim:

1. A new and distinct cultivar of *Longiflorum-Asiatic* hybrid lily plant, substantially as herein shown and described.

* * * * *